United States Patent [19]

Gough

[11] Patent Number: 4,627,906
[45] Date of Patent: Dec. 9, 1986

[54] ELECTROCHEMICAL SENSOR HAVING IMPROVED STABILITY

[75] Inventor: David A. Gough, Cardiff By the Sea, Calif.

[73] Assignee: The Regents of the University of California, Berkeley, Calif.

[21] Appl. No.: 768,125

[22] Filed: Aug. 22, 1985

Related U.S. Application Data

[63] Continuation of Ser. No. 538,123, Oct. 3, 1983, abandoned.

[51] Int. Cl.$^4$ ............................................. G01N 27/46
[52] U.S. Cl. .................................. 204/415; 204/412; 204/414; 204/418
[58] Field of Search ............... 204/412, 415, 414, 418, 204/432; 128/635

[56] References Cited

U.S. PATENT DOCUMENTS

| | | | |
|---|---|---|---|
| 3,260,656 | 7/1966 | Ros, Jr. ............................ | 204/415 X |
| 3,328,277 | 6/1967 | Solomons et al. .................. | 204/412 |
| 3,454,485 | 7/1969 | Hauk et al. ....................... | 204/415 X |
| 3,711,395 | 1/1973 | Plank et al. ....................... | 204/415 X |
| 3,756,923 | 9/1973 | Dahms ............................. | 204/412 X |
| 3,767,552 | 10/1973 | Lauer ............................... | 204/415 X |
| 4,025,412 | 5/1977 | LaConti ........................... | 204/426 X |
| 4,029,563 | 6/1977 | Binder et al. ...................... | 204/432 |
| 4,132,616 | 1/1979 | Tantram et al. ................... | 204/414 X |
| 4,168,220 | 9/1979 | McAdam et al. .................. | 204/412 X |
| 4,208,264 | 6/1980 | Polak et al. ....................... | 204/412 X |
| 4,293,399 | 10/1981 | Belanger et al. .................. | 204/415 X |
| 4,406,770 | 9/1983 | Chan et al. ........................ | 204/412 X |

Primary Examiner—John F. Niebling
Assistant Examiner—Nam X. Nguyen
Attorney, Agent, or Firm—Brown, Martin, Haller & Meador

[57] ABSTRACT

An electrochemical sensor device providing long term signal stability through a structure and relation of components effective to provide substantially uniform current flux at all points across a working electrode and a counter electrode of a three electrode system within an electrolyte container having a hydrophobic membrane permeable to a selected component to be measured and accessible to a fluid to be monitored.

9 Claims, 4 Drawing Figures

ELECTROCHEMICAL SENSOR HAVING IMPROVED STABILITY

FIELD OF THE INVENTION

This invention relates to an electrochemical sensor in which components are assembled in a relation having a stability particularly adapted for long term usage, such as chronic, in vivo implantation.

This invention was made with Government support under Grant No. AM 27541 awarded by the Department of Health and Human Services. The Government has certain rights in this invention.

This a continuation of application Ser. No. 538,123 filed Oct. 3, 1983, now abandoned.

BACKGROUND OF THE INVENTION

Electrochemical sensors for oxygen based on the Clark principle (Trans. Am. Soc. Inter. Organs, 2 41 (1956)), in which an oxygen permeable hydrophobic membrane separates an electrolyte-filled chamber containing working and reference electrodes from a liquid to be monitored, have been known for over twenty-five years. In these sensors, oxygen diffusing through the membrane to a platinum cathode is reduced and the current which flows as a result of this reduction is proportional to and is used as a measure of the concentration of oxygen in the liquid.

The signal generated by such sensors decays erratically during continuing use. That is, when sufficient current passes to cause the reference electrode to become polarized, the potential of the platinum electrode to which it is referenced is altered and/or positively charged ions from the reference electrodes migrate to the surface of the cathode rendering that surface ineffective for rapid oxygen reduction. This precludes long term or continuous use of the sensor except in situations where recalibration or compensation is possible.

Difficulties due to electrode polarization and ion migration have been reduced by means of a three electrode cell configuration used with a potentiostat electronic circuit, such as those described in U.S. patent to Galway et al, U.S. Pat. No. 4,227,998 dated Oct. 14, 1980 or U.S. patent to Stretter et al, U.S. Pat. No. 4,326,927 dated Apr. 27, 1982. In these arrangements, a working oxygen electrode, a potential reference electrode, and an indifferent counter electrode are connected in a circuit providing a high input impedance, e.g. one million ohms at the reference electrode so that only very small current, e.g. one billionth of an ampere or less can pass through the reference electrode and the potential of the reference electrode is not likely to drop or become polarized. Since the reference electrode is no longer a significant current pathway, a counter or auxiliary electrode is provided through which the oxygen dependent current passes. The potentiostat measures the voltage difference between the working electrode and the reference electrode, compares that to the desired voltage for rapid oxygen reduction and drives the current between the working electrode and the counter electrode until the voltage between the working and reference electrodes is as desired.

While the three electrode potentiostat system reduces difficulties due to polarization and ion migration, previously known electrochemical sensors have remained subject to lack of stability, erratic signal generation, and the development of electrode surface areas poisoned by adsorbed materials.

SUMMARY OF THE INVENTION

The electrochemical device of the present invention secures long term signal stability through a special novel structure and relation of components effective to provide substantially uniform current flux at all points across a working electrode and a counter electrode of a three-electrode system within an electrolyte container having a hydrophobic membrane permeable to a selected component to be measured and accessible to a fluid to be monitored.

DESCRIPTION OF PREFERRED EMBODIMENTS

Figure 1:
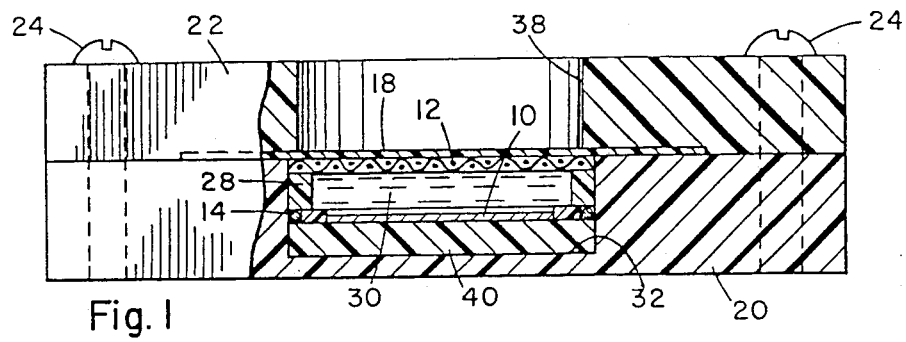
FIG. 1 is an elevational view, with parts broken away, of one embodiment of a sensing device according to the present invention.

The three-electrode sensing device of the present invention secures long sensor life and a signal stability through a novel construction and arrangement of electrodes 10, 12 and 14, electrolyte container 16, and hydrophobic permeable membrane 18 in which all points of the working electrode 10 are substantially evenly spaced from adjacent points of the counter electrode 12 and membrane 18.

In a first embodiment (see FIGS. 1 and 2), the electrolyte container 16 is shown as a pair of cooperating plates 20 and 22 of water insoluble nonconductive material which may be a plastic, such as Plexiglass, arranged to be secured together in face-to-face relation by fasteners 24 to retain a body 30 electrolyte and to hold the electrodes 10, 12 and 14, membrane 18 and spacers 26 and 28 in operational relationship immersed in the electrolyte. The back plate 20 is formed with a recess 32 which may be of circular or other symmetrical shape with a uniform depth sufficient to receive the electrodes, spacers and electrolyte and has fine channels 34 leading from the recess 32 to the exterior into which leads 36 to the electrodes are disposed. The channels are sealed around the leads 26 with a sealer such as Silastic, i.e. polydimethylsiloxane; and the leads are covered with waterproof insulation. The front plate 22 is formed with an opening 38 of substantially the same size and shape as the recess 32 disposed in alignment with the recess.

A resilient pad 40 of hydrophobic material, such as Silastic, with a shape for fitting snugly within the recess 32 is disposed against the bottom face of the recess and a working electrode 10 similar in shape to the recess 32, e.g. a circular disc of platinized platinum where the recess is circular, is placed with its back surface in intimate contact with and blocked off from the electrolyte by the surface of the pad 40. Preferably the diameter of the disc electrode 10, is slightly less than the diameter of the recess 32, to provide an annular space in which a reference electrode 14, which may be a thin chlorided silver ring slightly greater in diameter than the disc, is placed with a small separation between the two electrodes. The reference electrode should be as close as possible to the working electrode, ordinarily within 1 millimeter and preferably coplanar, so that it registers the true voltage more accurately than if it were at some position between the working electrode 10 and counter electrode 12.

A hydrophilic membrane spacer 26 of suitable material, such as Neflex, may be inserted in the space between the working and reference electrodes 10 and 14 to maintain the desired separation, but this is often not required.

It is desirable that the working electrode 10 be platinized as by electrochemical deposition of free dendrites on the surface of the platinum electrode to reduce any remaining problem of signal decay by increasing the real surface area of the electrode while the geometric surface remains unchanged. The increased surface area increases the rate of oxygen reduction on the electrode surface to the point at which the overall process approaches total diffusion limitation and is less subject to factors such as electrode poisoning that influence the rate of reaction. A roughness factor of two hundred, i.e. ration of real to geometric surface area, has been found to be useful.

A counter electrode 12 which may be of titanium, platinum or supported carbon having substantially the same geometric aspect as the working electrode 10, e.g. a disc, of screen or other open structure capable of providing free passage of components diffusing through the body 30 of electrolyte in the recess 32, is positioned just above in alignment with and parallel to the working electrode 10 and is held in this position by a spacer ring 28 of Silastic or other suitable material leaving a small disc-shaped volume filled with the body 30 of buffered electrolyte solution. A useful electrolyte solution may be, for example, an 0.1M KCl solution in a phosphate buffered aqueous liquid.

A thin hydrohobic membrane 18, which may be of Silastic or other material permeable to the components such as oxygen, to be measured extends across the top of the recess 32 with portions extending beyond the recess 32 clamped between the front and back plates 20 and 22 to retain electrolyte within the recess 32 in contact with the electrodes. One face of the membrane has access through the opening 38 in the front plate 22 to the fluid being monitored to allow permeation by the component to be measured of the monitored fluid and the other face in contact with the elctrolyte to pass that component into the electrolyte within the recess. It is desirable that the distance between the working electrode and the membrane surface in contact with the monitored fluid be small, e.g. 1 millimeter or less, to minimize response time, but may be greater, e.g. not more than about 3 millimeters, if longer response time is acceptable.

The uniform spacing of adjacent areas of the working electrode 10 and the counter electrode 12 secured in the structure is important to provide uniform current flux and avoid nonuniform electrochemical reaction which would encourage the formation of adsorbed species which would poison the electrode surfaces. For example, areas subjected to high density current flux may form a stubborn oxide of platinum that prevents further reduction of oxygen in those areas. Also, where the electrolyte includes a phosphate buffer, phosphate complexes may form on such areas.

Departure from this uniformity as, for example, in excessive overhang in edge portions where the size of one of two parallel electrodes is significantly larger than the other, should be avoided.

In general the coverage factor, e.g. the ratio between the shortest distance and the greatest distance between surface portions of the working electrode and counter electrode should be not less than 0.7 where the electrolyte concentration is in the range of, for example 0.1M KCl up to 0.3M KCl to insure uniform current flux, but the coverage factor becomes less critical at higher concentrations of electrolyte in the cell and, for example where the concentration is 0.5M KCl, a coverage factor as low as 0.4 may be useful.

Disposition of an open structure counter electrode 12 between the membrane 18 and the working electrode 10 in combination with a working electrode 10 of which all portions in contact with the electrolyte are substantially equidistant from the counter electrode 12 is an important factor in securing uniform current flux. Note that the resilient Silastic pad 40 blocks off the back of the working electrode 10 in the embodiment shown in FIGS. 1 and 2 so that the back surface does not provide active electrode portions unevenly spaced from the counter electrode 12. The open structure of the counter electrode 12 allows free diffusion of the component being measured from the membrane 18 to the working electrode 10 and location of the counter electrode 12 between the membrane 18 and the working electrode avoids the nonuniformity of diffusion path or of the electrode spacing which would result if the reverse relation were employed.

In a potentiostat arrangement for use in the present invention, (see FIG. 3) a working electrode 10 and a reference electrode 14 are connected to an operational amplifier 42 with a high input impedance shown as resistor 44 between the reference electrode 14 and the amplifier 42. The third or counter electrode 12 of the circuit has a low impedance, thus allowing the substantial current to pass between the working and counter electrodes 10 and 12 with the working electrode 10 maintained thereby at the desired potential with respect to the reference electrode 14. The applied reference potential is set by means of a rheostat 46 with a connection between the amplifier 42 and reference electrode 14 and is adjusted to set the potential between the reference electrode 14 and the working electrode 10 at a desired value. The amplifier 42 operates to drive the current between the working electrode 10 and the counter electrode 12 to establish and maintain the desired voltage between the working and reference electrode. The ammeter 48 measures current passing between the working electrode 10 and counter electrode 12 and hence, the rate of reaction at the electrode 10 of a component to be determined, e.g. reduction of oxygen at the working electrode. The current therefore is proportional to the concentration of that component in the monitored field.

Figure 4:
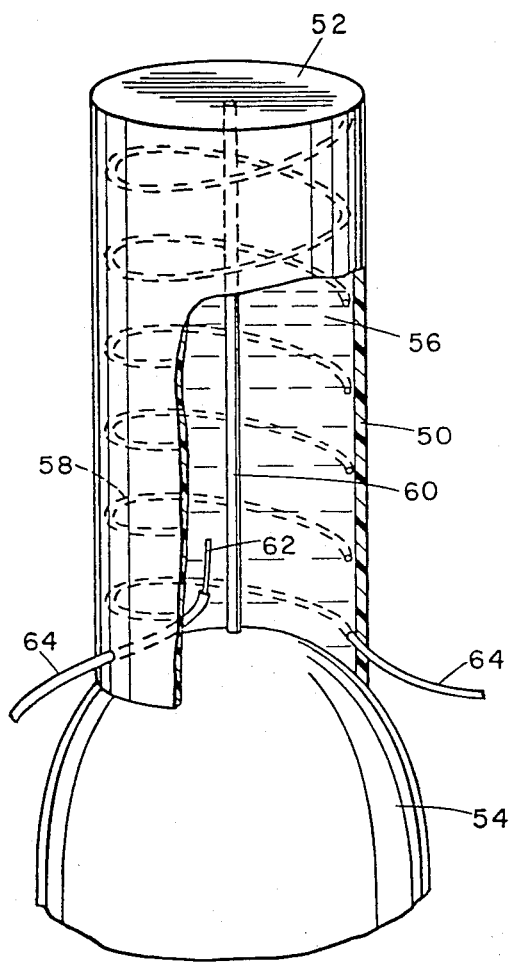
FIG. 4 is an elevational view, with parts broken away of a further embodiment of the sensing device of the present invention.

A second embodiment of the sensing device, shown in FIG. 4, employs a hydrophobic membrane cylinder 50 sealed with a cap 52 at one end and with an insulation body 54 at the other end to provide an electrolyte container surrounding a gelled or stiffened body 56 of electrolyte. A counter electrode 58 of cylindrical-shape and open structure is disposed adjacent the interior of the membrane 50. In the structure shown, the electrode 58 is a helical winding of titanium, platinum, or supported carbon, but a screen or an open deposit of these materials formed by sputtering or other procedure onto the interior membrane surface or onto gelled or stiffened body 56 of electrolyte could also be used.

The body of electrolyte may be stiffened by any of a variety of hydrophilic gelling or stiffening agents useful at the pH at which the electrolyte is maintained. Electrolytes at pH values in the range of from about pH1 to about pH8 may be stiffened by denatured collagen, e.g. gelatin, cross-linked with glutaraldehyde, polyacrylamide, agar, polyhydroxyethylmethacrylate, sodium carboxymethylcellulose, and the like. Generally, from about 25% to about 75% solids stiffening agents will be effective to provide the desired stiffness.

In this embodiment, the working electrode 60 is a cylinder which may be platinized platinum wire coaxial with the membrane 50 and counter electrode 58 extending between the cap 52 and the insulating body 54. Uniform coaxial spacing of the working electrode and counter electrode is maintained by the gelled or stiffened body of electrolyte.

As in the first embodiment, the distance between the membrane surface which will be in contact with a fluid to be monitored is preferably small, e.g. 1 millimeter or less to minimize response time, but may be greater, e.g. not more than about 3 millimeters, if longer response time is acceptable.

A reference electrode 62 of chlorided silver is disposed in the space between the working electrode 60 and the counter electrode 58.

Leads 64 to the counter electrode 58, working electrode 60, and reference electrode 62 extend through the insulating body 54.

The following examples are given to aid in understanding the invention, but it is to be understood that the invention is not limited to the dimensions, concentrations, or other details of the examples.

EXAMPLE 1

Figure 2:
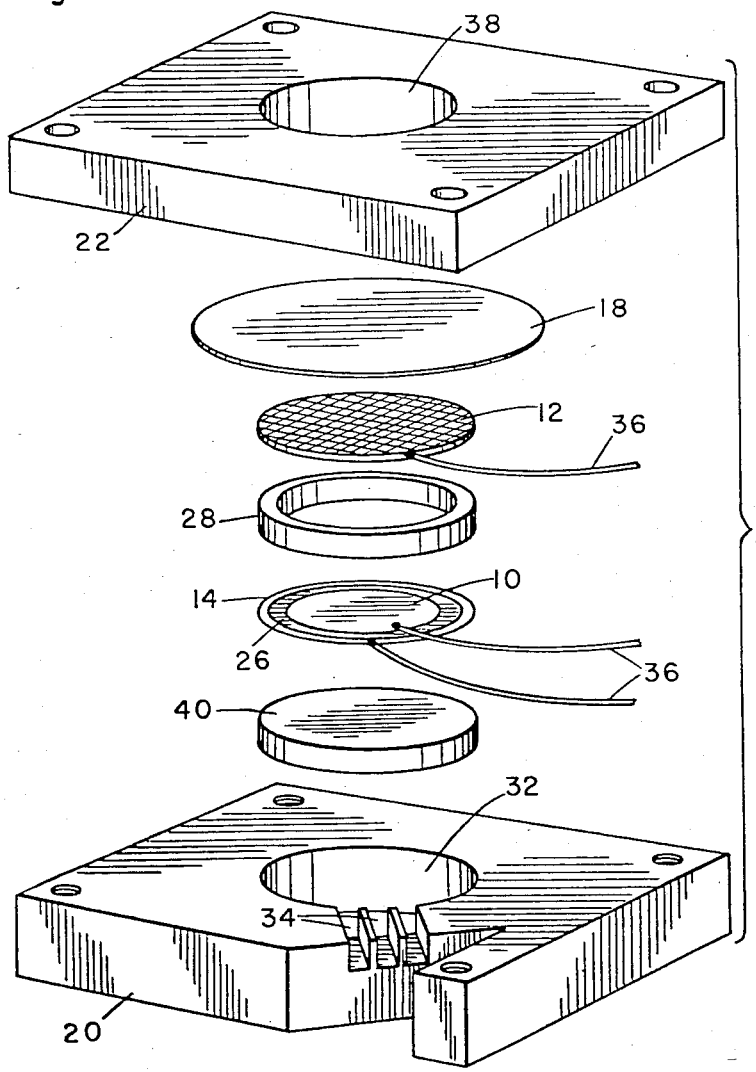
FIG. 2 is an exploded view of the sensing device of FIG. 1.

An electrochemical sensor as shown in FIGS. 1 and 2 was prepared in which the diameters of the recess, chlorided silver reference electrode, resilient pad, Neflex spacer ring, titanium screen counter electrode, and front plate opening were 1 centimeter; the diameter of the working electrode of 0.8 centimeters; the diameter of the hydrophobic Silastic membrane was 1.7 centimeters; and the depth of the recess was about 0.6 centimeters, and the recess was filled with phosphate buffered 0.1M KCl solution at pH7.3.

Distilled water was equilibrated by bubbling a mixture of $N_2$ and $O_2$ in the ratio occurring in the atmosphere and this water was placed in a beaker along with the sensor. The sensor was connected in a potentiostat circuit as shown in FIG. 4 and the beaker was was sealed.

Current generated in the circuit was 2 microamperes per square centimeter of working electrode area and this current was maintained within 5% for over one month continuous operation. The test was terminated by failure of power supply to the amplifier of the potentiometer circuit.

In a further test, the sensor was disposed in a sealed beaker with water which had been equilibrated with a mixture containing one-half the concentration of $O_2$ existing in the atmosphere. Current generated was 1 microampere per square centimeter of working electrode area and this current was also maintained substantially constant in continuous operation.

EXAMPLE 2

Figure 3:
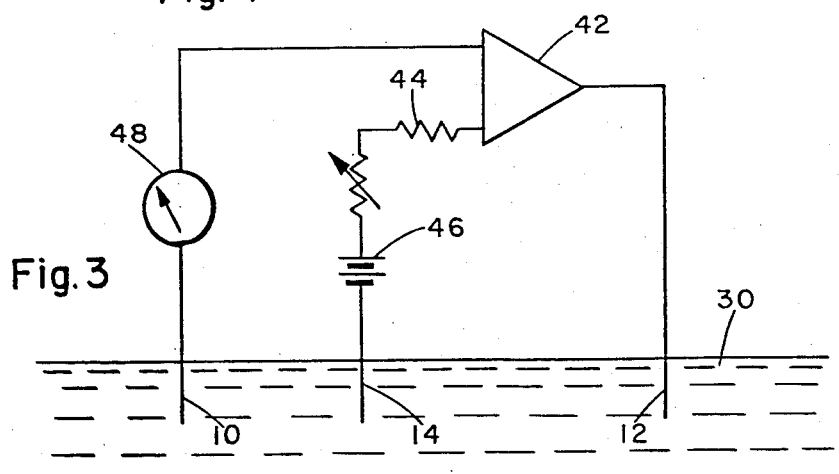
FIG. 3 is a schematic diagram of a potentiostat circuit for controlling operation of the sensing device.

An electrochemical sensor as shown in FIG. 3 was prepared in which the working electrode was a platinized platinum wire 0.005 inch in diameter and 1 centimeter long; the electrolyte was phosphate buffered 0.1M KCl solution, containing 50% solids of gelatin cross-linked with glutaraldehyde to form a cylinder of stiffened gel disposed within a cylindrical Silastic membrane having an outside diameter of 1 millimeter; the counter electrode was a helical coil of fine platinum wire with 0.5 millimeter between flights disposed adjacent the inner surface of the membrane and the reference electrode was a fine chlorided silver wire disposed between the working and counter electrodes.

In tests against equilibrated water, as in Example 1, the sensor generated a uniform current in continuous use.

I claim:

1. An electrochemical sensing device comprising an electrolyte container, an aqueous electrolyte in said container, a hollow cylindrical hydrophobic membrane forming a portion of said container and having a first outer surface accessible to a fluid to be monitored and a second inner surface accessible to said electrolyte, a cathode working electrode, a reference electrode and a counter electrode of cylindrical shape and open structure disposed adjacent the inner surface of said membrane and having its entire inner surface area exposed to and contacting said electrolyte in said container, said membrane being permeable to a component to be determined of said fluid, said counter electrode being coaxial with the interior of said membrane between said membrane and said working electrode and being constructed to allow free diffusion through it radially into said electrolyte and to said working electrode of said component to be determined, said working electrode being a rod extending along the axis of said cylindrical hydrophobic membrane and counter electrode along the entire length of said counter electrode and having all portions of it's surface in contact with said electrolyte and at a constant spacing from said counter electrode along the length of said cylindrical hydrophobic membrane to provide a substantially uniform current flux through the electrolyte between all points of said working electrode and opposed points of said counter electrode.

2. A sensor device as defined in claim 1 in which said cathode working electrode is constructed to consume the component to be determined and said counter electrode is constructed to be non-reactive to said component.

3. A sensor device as defined in claim 2 in which said counter electrode is a conductive screen.

4. A sensor device as defined in claim 1 in which the electrolyte concentration is in the range from about 0.1 molar to about 0.3 molar.

5. A sensor device as defined in claim 1 in which said counter electrode is a conductive helix adjacent the inner surface of said cylindrical hydrophobic membrane and extending substantially the entire length of said cylindrical hydrophobic membrane.

6. A sensor device as defined in claim 5 in which said electrolyte is a stiff hydrogel to aid in preserving the spacing of said electrodes.

7. A sensor device as defined in claim 6 in which the electrolyte concentration is in the range from 0.1 molar to about 0.3 molar, the pH is between about 1 to about 8, and said electrolyte is stiffened by a member of the group consisting of polyacrylamide, agar, polyhydroxyethyl methacrylate, sodium carboxy methyl cellulose, and collagen cross-linked with glutaraldehyde.

8. A sensing device as claimed in claim 1, further comprising:

a potentiostat circuit for maintaining a predetermined voltage between the reference and working electrodes and means for measuring a resultant current between said counter and working electrodes.

9. The sensing device as claimed in claim 8, wherein said potentiostat circuit comprises means for applying an adjustable reference potential to said reference electrode, comparator means having inputs connected to said working and reference electrodes for measuring a resultant potential difference between said electrodes and providing an output proportional to said potential difference, and means connecting the output of said comparator means to said counter electrode.

* * * * *